(12) United States Patent
Bilbe

(10) Patent No.: US 7,687,512 B2
(45) Date of Patent: Mar. 30, 2010

(54) USE OF PYRIDINYL-PYRIMIDINYLAMINO-BENZAMIDE DERIVATIVES FOR THE TREATMENT OF AMYLOID RELATED DISORDERS

(75) Inventor: Graeme Bilbe, Neuchâtel (CH)

(73) Assignee: Novartis AG, Basel (CH)

( * ) Notice: Subject to any disclaimer, the term of this patent is extended or adjusted under 35 U.S.C. 154(b) by 414 days.

(21) Appl. No.: 10/576,175

(22) PCT Filed: Oct. 26, 2004

(86) PCT No.: PCT/EP2004/012080

§ 371 (c)(1),
(2), (4) Date: Apr. 19, 2006

(87) PCT Pub. No.: WO2005/039586

PCT Pub. Date: May 6, 2005

(65) Prior Publication Data
US 2007/0129389 A1    Jun. 7, 2007

(30) Foreign Application Priority Data
Oct. 27, 2003    (GB) .................................. 0325031.3

(51) Int. Cl.
*A61K 31/506* (2006.01)
*A61P 25/00* (2006.01)
(52) U.S. Cl. .................. 514/275; 514/255.05
(58) Field of Classification Search ........... 514/275, 514/255; 544/331
See application file for complete search history.

(56) References Cited

FOREIGN PATENT DOCUMENTS

| EP | 0 588 762 | 3/1994 |
|---|---|---|
| WO | 95 09853 | 4/1995 |
| WO | 03 004488 | 1/2003 |
| WO | 03 057165 | 7/2003 |
| WO | 2004/005281 | 1/2004 |
| WO | 2004/029038 | 4/2004 |

OTHER PUBLICATIONS

Zimmermann et al., "Potent and selective inhibitors of the Abl-kinase: phenylamino-pyrimidine (PAP) derivatives," Bioorganic & Medicinal Chemistry Letters, Oxford, GB, vol. 7(2), pp. 187-192 (1997).

*Primary Examiner*—Sreeni Padmanabhan
*Assistant Examiner*—Sahar Javanmard
(74) *Attorney, Agent, or Firm*—Ann R. Pokalsky, Esq.; Dilworth & Barrese, LLP

(57) ABSTRACT

The invention relates to the use of an inhibitor of formula I

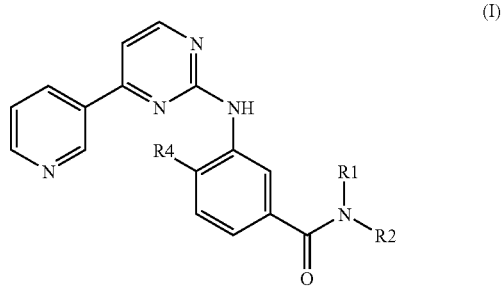

or a N-Oxide or a pharmaceutically acceptable salt thereof having an activity on protein kinases VEGFR-2, Tie-2, c-Src, c-Met, FGFR-1, Flt-1, HER-2, c-Abl, c-Raf, PDGFR-beta, c-Kit, or on a combination of the above enzymes, for the treatment and/or prevention of neurological and vascular disorders related to beta-amyloid generation and/or aggregation such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis

4 Claims, No Drawings

USE OF PYRIDINYL-PYRIMIDINYLAMINO-BENZAMIDE DERIVATIVES FOR THE TREATMENT OF AMYLOID RELATED DISORDERS

The invention relates to the use of compounds (hereinafter: "COMPOUND") or a N-Oxide or a pharmaceutically acceptable salt thereof having an activity on protein kinases VEGFR-2, Tie-2, c-Src, c-Met, FGFR-1, Flt-1, HER-2, c-Abl, c-Raf, PDGFR-beta, c-Kit, or on a combination of the above enzymes, for the treatment and/or prevention of neurological and vascular disorders related to beta-amyloid generation and/or aggregation such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis.

COMPOUND is preferably a compound of formula I

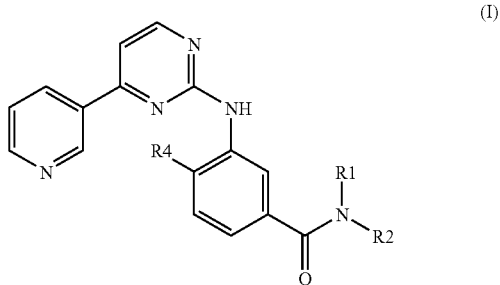

(I)

wherein $R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;

$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;

or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;

$R_4$ represents hydrogen, lower alkyl, or halogen;

Or more preferably COMPOUND is a compound selected from

4-Methyl-3-[[4-(3-pyridinyl)-2-pyrimidinyl]amino]benzamide,

4-Methyl-3-[[4-(3-pyridinyl)-2-pyrimidinyl]amino]benzanilide,

4-Methyl-N-(3-pyridinyl)-3-[[4-(3-pyridinyl)-2-pyrimidinyl]amino]benzamide,

N-(4-Chlorophenyl)-4-methyl-3-[[4-(3-pyridinyl)-2-pyrimidinyl]amino]benzamide,

2(R)- and 2(S)-[4-methyl-3-[[4-(3-pyridinyl)-2-pyrimidinyl]amino]benzoylamino]propanoic acid, 4-Methyl-3-[[4-(3-pyrdinyl)-2-pyrmidinyl]amino]-N-(8-quinolinyl)benzamide, 4-Methyl-3-[[4-(3-pyridinyl)-2-pyrimidinyl]amino]-N-(3-[trifluoromethoxy]phenyl)benzamide, 4-Methyl-3-[[4-(3-pyridinyl)-2-pyrimidinyl]amino]-N-(2-pyrrolidinoethyl)benzamide, 4-Methyl-3-[[4-(3-pyridinyl)-2-pyrimidinyl]amino]-N-(3-pyrrolidinophenyl)benzamide, 4-Methyl-3-[[4-(3-pyridinyl)-2-pyrimidinyl]amino]-N-(1-[2-pyrimidinyl]-4-piperidinyl)benzamide, N-(4-Di-[2-methoxyethyl]amino-3-trifluoromethylphenyl)-4-methyl-3-[[4-(3-pyridinyl)-2-pyrimidinyl]amino]benzamide, N-(4-[1H-Imidazolyl]-3-trifluoromethylphenyl)-4-methyl-3-[[4-(3-pyridinyl)-2-pyrimidinyl]amino]benzamide, 4-Methyl-3-[[4-(3-pyridinyl)-2-pyrimidinyl]amino]-N-(2-pyrrolidino-5-trifluoromethylphenyl)benzamide, N-(3,4-difluorophenyl)-4-methyl-3-[[4-(3-pyridinyl)-2-pyrimidinyl]amino]benzamide, 4-Methyl-3-[[4-(3-pyridinyl)-2-pyrimidinyl]amino]-N-(3-trifluoromethylbenzyl)benzamide, 4-Methyl-3-[[4-(3-pyridinyl)-2-pyrimidinyl]amino]-N-(3-trifluoromethylphenyl)benzamide, N-(3-Chloro-5-trifluoromethylphenyl)4-methyl-3-[[4-(3-pyridinyl)-2-pyrimidinyl]amino]benzamide, N-(4-Dimethylaminobutyl)4-methyl-3-[[4-(3-pyridinyl)-2-pyrimidinyl]amino]benzamide, 4-Methyl-N-[4-(4-methyl-1-piperazinyl)-3-trifluoromethylphenyl]-3-[[4-(3-pyridinyl)-2-pyrimidinyl]amino]benzamide, 4-Methyl-3-[[4-(3-pyridinyl)-2-pyrimidinyl]amino]-N-[4-(2,2,2-trifluoroethoxy)-3-trifluoromethylphenyl]benzamide, 4-Methyl-N-[4-(2-methyl-1H-imidazolyl)-3-trifluoromethylphenyl]-3-[[4-(3-pyridinyl)-2-pyrimidinyl]amino]benzamide, 4-Methyl-N-(4-phenyl-3-trifluoromethylphenyl)-3-[[4-(3-pyridinyl)-2-pyrimidinyl]amino]benzamide, 4-Methyl-N-[4-(4-methyl-1H-imidazolyl)-3-trifluoromethylphenyl]-3-[[4-(3-pyridinyl)-2-pyrimidinyl]amino]benzamide, Methyl 2(R) and 2(S)-[4-methyl-3-[[4-(3-pyridinyl)-2-pyrimidinyl]amino]benzoylamio]-3-[4-hydroxyphenyl]propanoate, N-[2-(N-Cyclohexyl-N-methylaminomethyl)phenyl]-4-methyl-3-[[4-(3-pyridinyl)-2-pyrimidinyl]amino]benzamide, N-[3-[2-(1H-Imidazolyl)ethoxy]phenyl]-4-methyl-3-[[4-(3-pyridinyl)-2-pyrimidinyl]amino]benzamide, 4-Methyl-N-[3-morpholino-5-trifluoromethylphenyl]-3-[[4-(3-pyridinyl)-2-pyrimidinyl]amino]benzamide, 4-Methyl-3-[[4-(3-pyrdnyl)-2-pyrimidinyl]amino]-N-(4-pyrrolidino-3-trifluoromethylphenyl)benzamide, 4-Methyl-3-[[4-(3-pyridinyl)-2-pyrimidinyl]amino]-N-(4-piperidino-3-trifluoromethylphenyl)benzamide, 4-Methyl-N-[4-morpholino-3-trifluoromethylphenyl]-3-[[4-(3-pyridinyl)-2-pyrimidinyl]amino]benzamide,
N-(4-Ethylamino-3-trifluoromethylphenyl)-4-methyl-3-[[4-(3-pyridinyl)-2-pyrimidinyl]amino]benzamide,
4-Methyl-3-[[4-(3-pyridinyl)-2-pyrimidinyl]amino]-N-(3-trifluoromethoxyphenyl)benzamide,
N-[4-(2-Hydroxypropylamino)-3-trifluoromethylphenyl]-4-methyl-3-[[4-(3-pyridinyl)-2-pyrimidinyl]amino]benzamide,
N-(4-Diethylamino-3-trifluoromethylphenyl)-4-methyl-3-[[4-(3-pyridinyl)-2-pyrimidinyl]amino]benzamide,
4-Methyl-3-[[4-(3-pyridinyl)-2-pyrimidinyl]amino]-N-[3-(3-pyridinyl)-5-trifluorophenyl]benzamide,
N-[3-[3-(1H-Imidazolyl)propoxy]phenyl]-4-methyl-3-[[4-(3-pyridinyl)-2-pyrimidinyl]amino]benzamide,
4-Methyl-3-[[4-(3-pyridinyl)-2-pyrimidinyl]amino]-N-[4-(3-pyridinyl)-3-trifluorophenyl]benzamide,
4-Methyl-N-[3-(4-methyl-1-piperazinyl)-5-trifluorophenyl]-3-[[4-(3-pyridinyl)-2-pyrimidinyl]amino]benzamide,
4-Methyl-N-[3-methylcarbamoyl-5-trifluorophenyl]-3-[[4-(3-pyridinyl)-2-pyrimidinyl]amino]benzamide,
4-Methyl-N-[3-methylcarbamoyl-5-morpholino]-3-[[4-(3-pyridinyl)-2-pyrimidinyl]amino]benzamide.

Further compounds which are even more particularly preferred are:
4-Methyl-3-[[4-(3-pyridinyl)-2-pyrimidinyl]amino]-N-[3-[3-(1H-imidazol-1-yl)propoxy]-phenyl]benzamide,
4-Methyl-3-[[4-(3-pyridinyl)-2-pyrimidinyl]amino]-N-[3-[2-(1H-imidazol-1-yl)ethoxy]phenyl]benzamide,
4-Methyl-3-[[4-(3-pyridinyl)-2-pyrimidinyl]amino]-N-[4-(ethylamino)-3-(trifluoromethyl)phenyl]benzamide,
4-Methyl-3-[[4-(3-pyridinyl)-2-pyrimidinyl]amino]-N-[4-(diethylamino)-3-(trifluoromethyl)phenyl]benzamide,
(±)-4-Methyl-3-[[4-(3-pyridinyl)-2-pyrimidinyl]amino]-N-[4-[(2-hydroxypropyl)amino]-3-(trifluoromethyl)phenyl]benzamide,
4-Methyl-3-[[4-(3-pyridinyl)-2-pyrimidinyl]amino]-N-[4-[bis(2-methoxyethyl)amino]-3-(trifluoromethyl)phenyl]benzamide,
4-Methyl-3-[[4-(3-pyridinyl)-2-pyrimidinyl]amino]-N-[4-(4-methyl-1-piperazinyl)-3-(trifluoromethyl)phenyl]benzamide,
4-Methyl-3-[[4-(3-pyridinyl)-2-pyrimidinyl]amino]-N-[4-(1-piperidinyl)-3-(trifluoromethyl)phenyl]benzamide,
4-Methyl-3-[[4-(3-pyridinyl)-2-pyrimidinyl]amino]-N-[4-(1-pyrrolidinyl)-3-(trifluoromethyl)phenyl]benzamide,
4-Methyl-3-[[4-(3-pyridinyl)-2-pyrimidinyl]amino]-N-[4-(4-morpholinyl)-3-(trifluoromethyl)phenyl]benzamide,
4-Methyl-3-[[4-(3-pyridinyl)-2-pyrimidinyl]amino]-N-[4-phenyl-3-(trifluoromethyl)phenyl]benzamide,
4-Methyl-3-[[4-(3-pyridinyl)-2-pyrimidinyl]amino]-N-[3-[4-(3-pyridinyl)-3-(trifluoromethyl)phenyl]methyl]benzamide,
4-Methyl-3-[[4-(3-pyridinyl)2-pyrimidinyl]amino]-N-[4-(1H-imidazol-1-yl)-3-(trifluoromethyl)phenyl]benzamide,
4-Methyl-3-[[4-(3-pyridinyl)-2-pyrimidinyl]amino]-N-[4-(2,4-dimethyl-1H-imidazol-1-yl)-3-(trifluoromethyl)phenyl]benzamide,
4-Methyl-3-[[4-(3-pyridinyl)-2-pyrimidinyl]amino]-N-[4-(4-methyl-1H-imidazol-1-yl)-3-(trifluoromethyl)phenyl]benzamide,
4-Methyl-3-[[4-(3-pyridinyl)-2-pyrimidinyl]amino]-N-[4-(2-methyl-1H-imidazol-1-yl)3-(trifluoromethyl)phenyl]benzamide,
4-Methyl-3-[[4-(3-pyridinyl)-2-pyrimidinyl]amino]-N-[3-(4-morpholinyl)-5-[(methylamino)carbonyl]phenyl]benzamide,
4-Methyl-3-[[4-(3-pyridinyl)-2-pyrimidinyl]amino]-N-[3-[(methylamino)carbonyl]-5-(trifluoromethyl)phenyl]benzamide,
4-Methyl-3-[[4-(3-pyridinyl)-2-pyrimidinyl]amino]-N-[5-(3-pyddinyl)-3-(trifluoromethyl)phenyl]benzamide,
4-Methyl-3-[[4-(3-pyridinyl)-2-pyrimidinyl]amino]-N-[5-(4-morpholinyl)-3-(trifluoromethyl)phenyl]benzamide,
4-Methyl-3-[[4-(3-pyridinyl)-2-pyrimidinyl]amino]-N-[5-(2-methyl-1H-imidazol-1-yl)-3-(trifluoromethyl)phenyl]benzamide,
4-Methyl-N-[3-(4-methyl-imidazol-1-yl)-5-trifluoromethyl-phenyl]-3-(4-pyridin-3-yl-pyrimidin-2-ylamino)-benzamide,
4-Methyl-3-[[4-(3-pyridinyl)-2-pyrimidinyl]amino]-N-[5-(5-methyl-1H-imidazol-1-yl)-3-(trifluoromethyl)phenyl]benzamide,
4-Methyl-3-[[4-(3-pyridinyl)-2-pyrimidinyl]amino]-N-[3-(4-methyl-1-piperazinyl)-5-(trifluoromethyl)phenyl]benzamide, and
4-Methyl-3-[[4-(3-pyridinyl)-2-pyrimidinyl]amino]-N-[2-(1-pyrrolidinyl)-5-(trifluoromethyl)phenyl]benzamide.

or most preferably COMPOUND is 4-Methyl-N-[3-(4-methyl-imidazol-1-yl)-5-trifluoromethyl-phenyl]-3-(4-pyridin-3-yl-pyrimidin-2-ylamino)-benzamide having the formula I

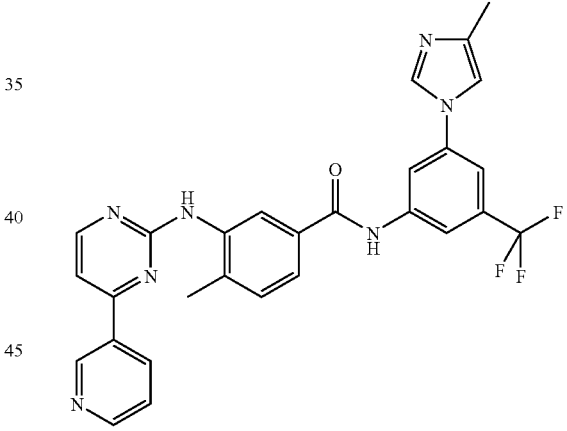

(I)

Compounds of formula I and methods for the preparation of such compounds are in particular generically and specifically disclosed in the patents and patent application PCT/EP03/07198, in particular in the compound claims and the final products of the working examples, the subject-matter of the final products, the pharmaceutical preparations and the claims is hereby incorporated into the present application by reference to this publication.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora (—B(OH)$_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substituents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$ alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substituents selected from the group defined above as substitutents for aryl, most preferably by lower alkyl, such as methyl, lower alkoxy, such as methoxy or ethoxy, or hydroxy. Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2;4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5pyrrolidinyl, piperidinyl, N-benzyl-4-piperidinyl, N-lower alkyl4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzene-sulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

VEGFR is vascular endothelial growth factor receptor.

FGFR is fibroblast growth factor receptor.

PDGFR is platelet-derived growth factor receptor.

The invention further relates to the use of COMPOUND or a N-Oxide or a pharmaceutically acceptable salt thereof for the manufacture of medicament having an activity on protein kinases VEGFR-2, Tie-2, c-Src, c-Met, FGFR-1, Fit-1, HER-2, c-Abl, c-Raf, PDGFR-beta, c-Kit, or on a combination of the above enzymes, for the treatment and/or prevention of neurological and vascular disorders related to beta-amyloid generation and/or aggregation such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis.

The invention also relates to a combination of COMPOUND or a pharmaceutically acceptable salt thereof with one or more drugs used for the treatment of neurological and vascular disorders related to beta-amyloid generation and/or aggregation such as neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis to treat warm-blooded animals including mammals, especially humans.

Depending on species, age, individual condition, mode of administration, and the clinical picture in question, effective doses, for example daily doses of about 10-1000 mg, preferably 10-50 mg or 50-200 or 200-400, especially 50-100 or 300-400 mg, are administered to warm-blooded animals of about 70 kg bodyweight. For adult patients with neurological and vascular disorders related to beta-amyloid generation and/or aggregation, especially neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis.

The invention relates likewise to a process or a method for the treatment of neurological and vascular disorders related to beta-amyloid generation and/or aggregation, especially neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis. The COMPOUNDS or N-oxides thereof can be administered as such or especially in the form of pharmaceutical compositions, prophylactically or therapeutically, preferably in an amount effective against the said diseases, to a warm-blooded animal, for example a human, requiring such treatment. In the case of an individual having a bodyweight of about 70 kg the daily dose administered is from approximately 0.01 g to approximately 5 g, preferably from approximately 0.25 g to approximately 1.5 g, more preferably 0.01 g to 0.05 g, even more preferably 0.025 g to 0.1 g most preferably 0.05 g to 1 g of a compound of the present invention.

The invention relates also to a method for administering to a human subject suffering from a neurological and vascular disorders related to beta-amyloid generation and/or aggregation, especially neurodegenerative diseases like Alzheimer's disease, Down's Syndrome, memory and cognitive impairment, dementia, amyloid neuropathies, brain inflammation, nerve and brain trauma, vascular amyloidosis, or cerebral hemorrhage with amyloidosis, COMPOUND or a pharmaceutically acceptable salt thereof, which comprises administering a pharmaceutically effective amount of COMPOUND or a pharmaceutically acceptable salt thereof to the human subject, preferably once daily for a period exceeding 3 months. The invention relates especially to such method wherein a daily dose of 200 to 800 mg, or 10 mg to 200 mg especially 400-600 mg or 10-100 mg, preferably 400 mg or 10-50 mg, of salt is administered.

The invention also relates in a combination which comprises (a) COMPOUND or a pharmaceutically acceptable salt thereof and (b) a therapeutic agent for the treatment of neurological and vascular disorders related to beta-amyloid generation and/or aggregation, most preferably a combination wherein the combination partners are present in synergistically effective amounts.

The effective dosage of each of the combination partners employed in the combination may vary depending on a variety of factors including the particular combination of the pharmaceutical compound partners, the route of administration, the severity of the disease, the renal and hepatic functions of the patient. The molar ratio (a)/(b) of the combination partners is about 0.1 to 10, most preferably 0.3 to 3 and the unit dosage form contains 20 to 200 mg, most preferably 50 to 150 mg of 4-Methyl-N-[3-(4-methyl-imidazol-1-yl)-5-trifluoromethyl-phenyl]-3-(4-pyridin-3-yl-pyrimidin-2-ylamino)-benzamide of the formula I.

EXAMPLE 1

Cell Culture

HEK/APPswe cells are plated in microtiter plates precoated with 10 µg/ml poly-D-lysine at 12,000 cells/well in 100 µl/well DMEM medium supplemented with 10% FCS, 0.25 mg/ml G418 sulfate, 1% penicillin streptomycin. The following day, supernatant is replaced with 90 µl/well of fresh medium and 10 µl/well of compound diluted in culture medium are added. Two types of control wells are used: cell culture medium without cells plus 10 µl/well of all compound dilutions (background signals) and cell culture medium from untreated cells (positive control). 24 hours later after compound addition, conditioned medium is collected and Aβ levels determined by a specific sandwich ELISA.

$A\beta_{40}$ and $A\beta_{42}$ Detection by Sandwich ELISA

For the sandwich ELISA, the maxisorp microtiterplates are coated overnight at 4° C. with 100 µl/well of the monoclonal antibody 25H10 diluted 1:1000 in PB for $A\beta_{40}$ detection or monoclonal antibody B10E7 diluted 1:2750 for detection of $A\beta_{42}$. Wells are then emptied, washed three times with 350 µl PBS and blocking is performed for 2 hours at room temperature with 200 µl/well of 2% BSA, 0.05% Tween20 in PBS. After washing the wells as described above, 10 µl of the conditioned media samples to be tested are added to wells containing 90 µl of medium and 0.18 µg/ml of biotinylated monoclonal β1 antibody and incubated overnight at 4° C. Wells were washed as described above and 100 µl/well of alkaline phosphatase coupled to streptavidin diluted 1:5,000 in medium are added. After 1 hour incubation at room temperature wells are washed as described above and alkaline phosphatase activity is determined by adding 100 µl/well of diethanolamine buffer, pH 9.8 (100 mM diethanolamine, 1 mM $MgCl_2$, pH adjusted to 9.8 with 2 M HCl) containing the chemiluminescent CSPD substrate (25 mM stock solution diluted 1:416) and the enhancer Emerald II (diluted 1:10). After 15 minutes incubation at room temperature in the dark, plates are measured on the luminometer (Analyst AD; LJL Biosystems, USA $A\beta_{40}$). Values are given as % reduction of A β. The 100% reduction value is calculated from a series of wells containing only medium and extract and the 0% reduction value from conditioned medium only. Samples are measured in triplicate. A reference compound is included in all plates as control for assay performance.

MTS Assay

To determine cytotoxicity, cells are tested by the MTS colorimetric kit performed essentially according to the manufacturer's specifications (Promega, #G5430X). After collecting the conditioned medium for the sandwich ELISA, the rest of the conditioned medium is removed completely and replaced with 100 µl/well culture medium containing one fifth of MTS solution prepared as recommended in the kit. After 3 hours incubation at 37° C., absorbance is read at an OD of 490 nm with a reference wavelength set to 630 nm. Values are given as % metabolic rate (n=6). The 0% value is calculated from wells which had no cells, 100% from wells with an untreated cell layer

EXAMPLE 2

4-Methyl-N-[3-(4-methyl-imidazol-1-yl)-5-trifluoromethyl-phenyl]-3-(4-pyridin-3-yl-pyrimidin-2-ylamino)-benzamide

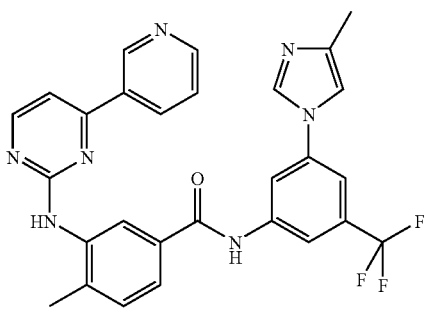

This compound has the following activities in cell-free enzyme assays:

| | |
|---|---|
| VEGFR-2 | 3.2 microM |
| Tie-2 | 4.6 microM |
| c-Src | 4.6 microM |
| c-Met | 4.7 microM |
| FGFR-1 | 6.7 microM |
| Flt-1 | 7.7 microM |
| HER-2 | 7.2 microM |
| c-Abl | 295 nM |
| c-Raf-1 | 1.1 microM |
| PDGFR-beta | 5.8 microM |
| c-Kit | 7.8 microM |

The compound of example 1 demonstrated a clear reduction of Abeta secretion in the medium of HEK/APPswe cell cultures at concentrations below 10 microM, without having any effect on cellular viability.

The invention claimed is:

1. A method for the treatment of neurological and vascular disorders related to beta-amyloid generation and/or aggregation selected from Alzheimer's disease. Down's Syndrome. memory and cognitive impairment, dementia, amyloid neuropathies, brain inflammation, nerve and brain trauma, vascular amyloidosis, and cerebral hemorrhage with amyloidosis, said method comprising administering an effective amount of 4-Methyl-N-[3-(4-methyl-imidazol-1-yl)-5-trifluoromethyl-phenyl]-3-(4-pyridin-3-yl-pyrimidin-2-ylamino)-benzamide; or a pharmaceutically acceptable salt thereof.

2. A method according to claim 1 wherein a daily dose of 10 to 800 mg of a compound is administered to an adult human.

3. A method according to claim 1 wherein the disease to be treated is Alzheimer's disease.

4. A method of treating mammals suffering from neurological and vascular disorders related to beta-amyloid generation and/or aggregation selected from Alzheimer's disease, Down's Syndrome, memory and cognitive impairment, dementia, amyloid neuropathies, brain inflammation, nerve and brain trauma, vascular amyloidosis, and cerebral hemorrhage with amyloidosis, said method comprising administering an effective amount of 4-Methyl-N-[3-(4-methyl-imidazol-1-yl)-5-trifluoromethyl-phenyl]-3-(4-pyridin-3-yl-pyrimidin-2-ylamino)-benzamide of formula I

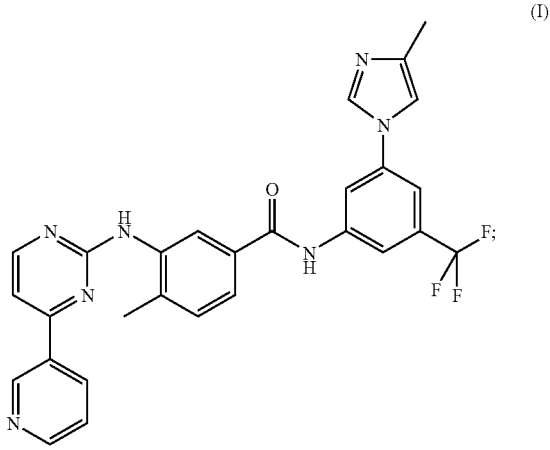

(I)

or a pharmaceutically acceptable salt thereof.

* * * * *